United States Patent
Jacobs et al.

(10) Patent No.: US 7,128,740 B2
(45) Date of Patent: Oct. 31, 2006

(54) METHOD FOR INTERRUPTING CONDUCTION PATHS WITHIN THE HEART

(76) Inventors: Clemens J. Jacobs, Veenlanden 40, 3871 RD, Hoevelaken (NL); Tjong Hauw Sie, Prinses Julianastraat 49, 8019 AT, Zwolle (NL)

(*) Notice: Subject to any disclaimer, the term of this patent is extended or adjusted under 35 U.S.C. 154(b) by 190 days.

(21) Appl. No.: 10/405,392

(22) Filed: Apr. 2, 2003

(65) Prior Publication Data

US 2003/0191462 A1   Oct. 9, 2003

Related U.S. Application Data

(60) Continuation of application No. 10/277,144, filed on Oct. 21, 2002, now abandoned, which is a continuation of application No. 09/583,303, filed on May 30, 2000, now Pat. No. 6,502,575, which is a division of application No. 09/180,124, filed as application No. PCT/NL97/00223 on Apr. 25, 1997, now Pat. No. 6,165,174.

(30) Foreign Application Priority Data

May 3, 1996   (NL) .................................. 1003024

(51) Int. Cl.
   *A61B 18/18* (2006.01)
   *A61B 19/00* (2006.01)

(52) U.S. Cl. .................. 606/41; 607/122; 128/898
(58) Field of Classification Search .................. 606/41, 606/42, 45, 46, 48–50; 607/100–105, 122; 128/898
See application file for complete search history.

(56) References Cited

U.S. PATENT DOCUMENTS

| | | |
|---|---|---|
| 3,736,936 A | 6/1973 | Basiulis et al. |
| 3,807,403 A | 4/1974 | Stumpf et al. |
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |
| 3,859,986 A | 1/1975 | Okada et al. |
| 3,862,627 A | 1/1975 | Hans, Sr. |
| 3,886,945 A | 6/1975 | Stumpf et al. |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |

(Continued)

FOREIGN PATENT DOCUMENTS

DE   9417787.2 U1   2/1995

(Continued)

OTHER PUBLICATIONS

Elvan et al, "Radiofrequency Catheter Ablation of the Atria Reduces Inducibility and Duration of Atrial Fibrillation in Dogs", Circulation, vol. 91, No. 8, Apr. 15, 1995, pp. 2235-2244.

(Continued)

*Primary Examiner*—Michael Peffley
(74) *Attorney, Agent, or Firm*—Akerman Senterfitt

(57) ABSTRACT

A method for making transmural lesions in one or more walls of the atria of the heart in open-heart surgery. The lesion blocks electrical impulses in a direction crosswise to the lesion. The method uses a probe having a handle (1), a closed electrode (2) at an end of the probe, a relatively rigid member (5) of physiologically acceptable plastic connecting the probe and the electrode, and means (6, 7) for coupling the probe to an RF power source.

29 Claims, 3 Drawing Sheets

U.S. PATENT DOCUMENTS

| | | |
|---|---|---|
| 4,022,215 A | 5/1977 | Benson |
| 4,061,135 A | 12/1977 | Widran et al. |
| 4,063,560 A | 12/1977 | Thomas et al. |
| 4,072,152 A | 2/1978 | Linehan |
| 4,082,096 A | 4/1978 | Benson |
| 4,207,897 A | 6/1980 | Lloyd et al. |
| 4,248,224 A | 2/1981 | Jones |
| 4,275,734 A | 6/1981 | Mitchiner |
| 4,278,090 A | 7/1981 | van Gerven |
| 4,377,168 A | 3/1983 | Rzasa et al. |
| 4,519,389 A | 5/1985 | Gudkin et al. |
| 4,562,838 A | 1/1986 | Walker |
| 4,598,698 A | 7/1986 | Siegmund |
| 4,601,290 A | 7/1986 | Effron et al. |
| 4,664,110 A | 5/1987 | Schanzlin |
| 4,736,749 A | 4/1988 | Lundback |
| 4,779,611 A | 10/1988 | Grooters et al. |
| 4,802,475 A | 2/1989 | Weshahy |
| 4,815,470 A | 3/1989 | Curtis et al. |
| 4,872,346 A | 10/1989 | Kelly-Fry et al. |
| 4,916,922 A | 4/1990 | Mullens |
| 4,917,095 A | 4/1990 | Fry et al. |
| 4,920,978 A | 5/1990 | Colvin |
| 4,936,281 A | 6/1990 | Stasz |
| 4,946,460 A | 8/1990 | Merry et al. |
| 5,013,312 A | 5/1991 | Parins et al. |
| 5,029,574 A | 7/1991 | Shimamura et al. |
| 5,044,165 A | 9/1991 | Linner et al. |
| 5,078,713 A | 1/1992 | Varney |
| 5,080,102 A | 1/1992 | Dory |
| 5,080,660 A | 1/1992 | Buelna |
| 5,100,388 A | 3/1992 | Behl et al. |
| 5,108,390 A | 4/1992 | Potocky et al. |
| 5,147,355 A | 9/1992 | Friedman et al. |
| 5,167,659 A | 12/1992 | Ohtomo et al. |
| 5,178,133 A | 1/1993 | Pena |
| 5,207,674 A | 5/1993 | Hamilton |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,246,440 A | 9/1993 | Van Noord |
| 5,254,116 A | 10/1993 | Baust et al. |
| 5,263,493 A | 11/1993 | Avitall |
| 5,269,291 A | 12/1993 | Carter |
| 5,275,595 A | 1/1994 | Dobak, III |
| 5,277,201 A | 1/1994 | Stern |
| 5,277,696 A | 1/1994 | Hagen |
| 5,281,213 A | 1/1994 | Milder et al. |
| 5,281,215 A | 1/1994 | Milder |
| 5,295,484 A | 3/1994 | Marcus et al. |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,334,181 A | 8/1994 | Rubinsky et al. |
| 5,334,193 A | 8/1994 | Nardella |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,385,148 A | 1/1995 | Lesh et al. |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,423,807 A | 6/1995 | Milder |
| 5,423,811 A | 6/1995 | Imran et al. |
| 5,427,119 A | 6/1995 | Swartz et al. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,443,463 A | 8/1995 | Stern et al. |
| 5,443,470 A | 8/1995 | Stern et al. |
| 5,450,843 A | 9/1995 | Moll et al. |
| 5,452,582 A | 9/1995 | Longsworth |
| 5,452,733 A | 9/1995 | Sterman et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,522,873 A | 6/1996 | Jackman et al. |
| 5,536,267 A | 7/1996 | Edwards et al. |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,558,671 A | 9/1996 | Yates |
| 5,560,362 A | 10/1996 | Sliwa, Jr. et al. |
| 5,562,720 A | 10/1996 | Stern et al. |
| 5,569,241 A | 10/1996 | Edwards |
| 5,571,088 A | 11/1996 | Lennox et al. |
| 5,571,215 A | 11/1996 | Sterman et al. |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |
| 5,605,539 A | 2/1997 | Buelna et al. |
| 5,607,462 A | 3/1997 | Imran |
| 5,609,151 A * | 3/1997 | Mulier et al. ............... 600/373 |
| 5,617,854 A | 4/1997 | Munsif |
| 5,630,837 A | 5/1997 | Crowley |
| 5,637,090 A | 6/1997 | McGee et al. |
| 5,643,197 A | 7/1997 | Brucker et al. |
| 5,656,029 A | 8/1997 | Imran et al. |
| 5,658,278 A | 8/1997 | Imran et al. |
| 5,671,747 A | 9/1997 | Connor |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | LaFontaine |
| 5,678,550 A | 10/1997 | Bassen et al. |
| 5,680,860 A | 10/1997 | Imran |
| 5,681,278 A | 10/1997 | Igo et al. |

| | | | | | | |
|---|---|---|---|---|---|---|
| 5,681,308 A | 10/1997 | Edwards et al. | | 5,993,447 A | 11/1999 | Blewett et al. |
| 5,687,723 A | 11/1997 | Avitall | | 6,007,499 A | 12/1999 | Martin et al. |
| 5,687,737 A | 11/1997 | Branham et al. | | 6,012,457 A | 1/2000 | Lesh |
| 5,688,267 A | 11/1997 | Panescu et al. | | 6,016,811 A | 1/2000 | Knopp et al. |
| 5,690,611 A | 11/1997 | Swartz et al. | | 6,042,556 A | 3/2000 | Beach et al. |
| 5,697,536 A | 12/1997 | Eggers et al. | | 6,063,081 A | 5/2000 | Mulier et al. |
| 5,697,882 A | 12/1997 | Eggers et al. | | 6,071,279 A | 6/2000 | Whayne et al. |
| 5,697,925 A | 12/1997 | Taylor | | 6,088,894 A | 7/2000 | Oakley |
| 5,697,927 A | 12/1997 | Imran et al. | | 6,096,037 A | 8/2000 | Mulier |
| 5,697,928 A | 12/1997 | Walcott et al. | | 6,113,592 A | 9/2000 | Taylor |
| 5,713,942 A | 2/1998 | Stern | | 6,117,101 A | 9/2000 | Diederich et al. |
| 5,716,389 A | 2/1998 | Walinsky et al. | | 6,120,496 A | 9/2000 | Whayne et al. |
| 5,718,241 A | 2/1998 | Ben-Haim et al. | | 6,142,993 A | 11/2000 | Whayne et al. |
| 5,718,701 A | 2/1998 | Shai et al. | | 6,142,994 A | 11/2000 | Swanson et al. |
| 5,720,775 A | 2/1998 | Larnard | | 6,152,920 A | 11/2000 | Thompson et al. |
| 5,722,402 A | 3/1998 | Swanson et al. | | 6,161,543 A | 12/2000 | Cox et al. |
| 5,730,074 A | 3/1998 | Peter | | 6,165,174 A | 12/2000 | Jacobs et al. |
| 5,730,127 A | 3/1998 | Avitall | | 6,217,528 B1 | 4/2001 | Koblish et al. |
| 5,730,704 A | 3/1998 | Avitall | | 6,217,576 B1 | 4/2001 | Tu et al. |
| 5,733,280 A | 3/1998 | Avitall | | 6,224,592 B1 | 5/2001 | Eggers et al. |
| 5,735,280 A | 4/1998 | Sherman et al. | | 6,231,518 B1 | 5/2001 | Grabek et al. |
| 5,735,290 A | 4/1998 | Sterman et al. | | 6,235,024 B1 | 5/2001 | Tu |
| 5,755,760 A | 5/1998 | Maguire et al. | | 6,237,605 B1 | 5/2001 | Vaska et al. |
| 5,769,846 A | 6/1998 | Edwards et al. | | 6,238,347 B1 | 5/2001 | Nix et al. |
| 5,782,828 A | 7/1998 | Chen et al. | | 6,238,393 B1 | 5/2001 | Mulier |
| 5,785,706 A | 7/1998 | Bednarek | | 6,245,061 B1 | 6/2001 | Panescu et al. |
| 5,788,636 A | 8/1998 | Curley | | 6,245,064 B1 | 6/2001 | Lesh et al. |
| 5,792,140 A | 8/1998 | Tu et al. | | 6,245,065 B1 | 6/2001 | Panescu et al. |
| 5,797,960 A | 8/1998 | Stevens et al. | | 6,251,092 B1 | 6/2001 | Qin et al. |
| 5,800,428 A | 9/1998 | Nelson et al. | | 6,251,128 B1 | 6/2001 | Knopp et al. |
| 5,800,482 A | 9/1998 | Pomeranz et al. | | 6,270,471 B1 | 8/2001 | Hechel et al. |
| 5,810,802 A | 9/1998 | Panescu et al. | | 6,290,699 B1 * | 9/2001 | Hall et al. .................. 606/41 |
| 5,823,956 A | 10/1998 | Roth et al. | | 6,293,943 B1 | 9/2001 | Panescu et al. |
| 5,827,216 A | 10/1998 | Igo et al. | | 6,296,619 B1 | 10/2001 | Brisken et al. |
| 5,836,947 A | 11/1998 | Fleischman et al. | | 6,302,880 B1 | 10/2001 | Schaer |
| 5,840,030 A | 11/1998 | Ferek-Petric et al. | | 6,311,692 B1 | 11/2001 | Vaska et al. |
| 5,844,349 A | 12/1998 | Oakley et al. | | 6,312,383 B1 | 11/2001 | Lizzi et al. |
| 5,846,187 A | 12/1998 | Wells et al. | | 6,314,962 B1 | 11/2001 | Vaska et al. |
| 5,846,191 A | 12/1998 | Wells et al. | | 6,314,963 B1 | 11/2001 | Vaska et al. |
| 5,849,028 A | 12/1998 | Chen | | 6,325,797 B1 | 12/2001 | Stewart et al. |
| 5,860,951 A | 1/1999 | Eggers et al. | | 6,328,736 B1 | 12/2001 | Mulier et al. |
| 5,871,523 A | 2/1999 | Fleischman et al. | | 6,332,881 B1 | 12/2001 | Carner et al. |
| 5,871,525 A | 2/1999 | Edwards et al. | | 6,358,248 B1 | 3/2002 | Mulier et al. |
| 5,873,845 A | 2/1999 | Cline et al. | | 6,361,531 B1 | 3/2002 | Hissong |
| 5,876,399 A | 3/1999 | Chia et al. | | 6,364,876 B1 | 4/2002 | Erb et al. |
| 5,879,295 A | 3/1999 | Li et al. | | 6,368,275 B1 | 4/2002 | Sliwa et al. |
| 5,879,296 A | 3/1999 | Ockuly et al. | | 6,371,955 B1 | 4/2002 | Fuimaono et al. |
| 5,881,732 A | 3/1999 | Sung et al. | | 6,383,151 B1 | 5/2002 | Diederich et al. |
| 5,882,346 A | 3/1999 | Pomeranz et al. | | 6,385,472 B1 | 5/2002 | Hall et al. |
| 5,885,278 A | 3/1999 | Fleischman | | 6,398,792 B1 | 6/2002 | O'Connor |
| 5,893,848 A | 4/1999 | Negus et al. | | 6,409,722 B1 | 6/2002 | Hoey |
| 5,895,417 A | 4/1999 | Pomeranz et al. | | 6,413,254 B1 | 7/2002 | Hissong et al. |
| 5,897,553 A * | 4/1999 | Mulier et al. ................ 606/41 | | 6,419,648 B1 | 7/2002 | Vitek et al. |
| 5,897,554 A | 4/1999 | Chia et al. | | 6,425,867 B1 | 7/2002 | Vaezy et al. |
| 5,899,898 A | 5/1999 | Arless et al. | | 6,430,426 B1 | 8/2002 | Avitall |
| 5,899,899 A | 5/1999 | Arless et al. | | 6,440,130 B1 | 8/2002 | Mulier |
| 5,902,289 A | 5/1999 | Swartz et al. | | 6,443,952 B1 | 9/2002 | Mulier |
| 5,904,711 A | 5/1999 | Flom et al. | | 6,447,507 B1 | 9/2002 | Bednarek et al. |
| 5,906,580 A | 5/1999 | Kline-Schoder et al. | | 6,461,314 B1 | 10/2002 | Pant et al. |
| 5,906,587 A | 5/1999 | Zimmon | | 6,461,956 B1 | 10/2002 | Hsuan et al. |
| 5,906,606 A | 5/1999 | Chee et al. | | 6,464,700 B1 | 10/2002 | Koblish et al. |
| 5,908,029 A | 6/1999 | Knudson et al. | | 6,471,697 B1 | 10/2002 | Lesh |
| 5,916,213 A | 6/1999 | Haissaguerre et al. | | 6,471,698 B1 | 10/2002 | Edwards et al. |
| 5,916,214 A | 6/1999 | Cosio et al. | | 6,474,340 B1 | 11/2002 | Vaska et al. |
| 5,921,924 A | 7/1999 | Avitall | | 6,475,216 B1 | 11/2002 | Mulier |
| 5,921,982 A | 7/1999 | Lesh et al. | | 6,477,396 B1 | 11/2002 | Mest et al. |
| 5,927,284 A | 7/1999 | Borst et al. | | 6,484,727 B1 | 11/2002 | Vaska et al. |
| 5,931,810 A | 8/1999 | Grabek | | 6,488,680 B1 | 12/2002 | Francischelli |
| 5,931,848 A | 8/1999 | Saadat | | 6,502,575 B1 | 1/2003 | Jacobs et al. |
| 5,928,191 A | 9/1999 | Houser et al. | | 6,514,250 B1 | 2/2003 | Jahns |
| 5,954,661 A | 9/1999 | Greenspon et al. | | 6,527,767 B1 | 3/2003 | Wang et al. |
| 5,971,980 A | 10/1999 | Sherman | | 6,537,248 B1 | 3/2003 | Mulier |
| 5,971,983 A | 10/1999 | Lesh | | 6,537,272 B1 | 3/2003 | Christopherson et al. |

| | | |
|---|---|---|
| 6,558,382 B1 | 5/2003 | Jahns |
| 6,584,360 B1 | 6/2003 | Francischelli |
| 6,585,732 B1 | 7/2003 | Mulier et al. |
| 6,605,084 B1 | 8/2003 | Acker et al. |
| 6,610,055 B1 | 8/2003 | Swanson et al. |
| 6,610,060 B1 | 8/2003 | Mulier |
| 6,613,048 B1 | 9/2003 | Mulier |
| 6,645,199 B1 | 11/2003 | Jenkins et al. |
| 6,648,883 B1 | 11/2003 | Francischelli |
| 6,656,175 B1 | 12/2003 | Francischelli |
| 6,663,627 B1 | 12/2003 | Francischelli |
| 6,692,450 B1 | 2/2004 | Coleman |
| 6,699,240 B1 | 3/2004 | Francischelli |
| 6,702,811 B1 | 3/2004 | Stewart et al. |
| 6,706,038 B1 | 3/2004 | Francischelli |
| 6,706,039 B1 | 3/2004 | Mulier |
| 6,716,211 B1 | 4/2004 | Mulier et al. |
| 6,736,810 B1 | 5/2004 | Hoey |
| 6,755,827 B1 | 6/2004 | Mulier |
| 6,764,487 B1 | 7/2004 | Mulier |
| 6,773,433 B1 | 8/2004 | Stewart et al. |
| 6,776,780 B1 | 8/2004 | Mulier |
| 6,807,968 B1 | 10/2004 | Francischelli |
| 6,827,715 B1 | 12/2004 | Francischelli |
| 6,849,073 B1 | 2/2005 | Hoey |
| 6,858,028 B1 | 2/2005 | Mulier |
| 6,887,238 B1 | 5/2005 | Jahns |
| 6,899,711 B1 | 5/2005 | Stewart et al. |
| 6,911,019 B1 | 6/2005 | Mulier |
| 6,916,318 B1 | 7/2005 | Francischelli |
| 6,936,046 B1 | 8/2005 | Hissong |
| 6,949,097 B1 | 9/2005 | Stewart et al. |
| 6,949,098 B1 | 9/2005 | Mulier |
| 6,960,205 B1 | 11/2005 | Jahns |
| 6,962,589 B1 | 11/2005 | Mulier |
| 2003/0045872 A1 | 3/2003 | Jacobs |
| 2003/0144656 A1 | 7/2003 | Ocel |
| 2003/0191462 A1 | 10/2003 | Jacobs |
| 2003/0216724 A1 | 11/2003 | Jahns |
| 2004/0015106 A1 | 1/2004 | Coleman |
| 2004/0015219 A1 | 1/2004 | Francischelli |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0143729 A1 | 6/2005 | Francischelli |
| 2005/0165392 A1 | 7/2005 | Francischelli |
| 2005/0209564 A1 | 9/2005 | Bonner |
| 2005/0256522 A1 | 11/2005 | Francischelli |
| 2005/0267454 A1 | 12/2005 | Hissong |
| 2006/0009756 A1 | 1/2006 | Francischelli |
| 2006/0009759 A1 | 1/2006 | Christian |

FOREIGN PATENT DOCUMENTS

| | | |
|---|---|---|
| EP | 0 280 972 A1 | 9/1988 |
| WO | WO-95/03742 A1 | 2/1995 |
| WO | WO-95/17222 A1 | 6/1995 |
| WO | WO-95/19148 A1 | 7/1995 |
| WO | WO-97/16127 A1 | 5/1997 |

OTHER PUBLICATIONS

Avitall et al, "A Thorascopic Approach to Ablate Atrial Fibrillation Via Linear Radiofrequency Lesion Generation on the Epicardium of Both Atria", NAPSE Abstracts, PACE, vol. 19, No. 241, Apr. 1996.

Cox, J.L. et al, "Surgical Interruption of Atrial Reentry as a Cure for Atrial Fibrillation", Atrial Fibrillation: Mechanisms and Therapeutic Strategies, Futura Publishing Co., Inc., Armonk, NY, 1994, pp. 373-404.

Chitwood, "Will c. Sealy, MD: The Father of Arrhythmia Surgery—The Story of the Fisherman with a Fast Pulse," Annals of Thoracic Surgery 58:1228-1239, 1994.

Gallagher et al., "Cryosurgical Ablation of Accessory Atrioventrical Connections: A Method for Corrections of the Pre-excitation Syndrome," Circulation 55(3): 471-479, 1977.

Sealy, "Direct Surgical Treatment of Arrhythmias: The Last Frontier in Surgical Cardiology," Chest 75(5): 536-537, 1979.

Sealy, "The Evolution of the Surgical Methods for Interruption of Right Free Wall Kent Bundles," The Annals of Thoracic Surgery 36(1): 29-36, 1983.

Guiraudon et al., "Surgical Repair of Wolff-Parkinson-White Syndrome: A New Closed-Heart Technique," The Annals of Thoracic Surgery 37(1): 67-71, 1984.

Klein et al., "Surgical Correction of the Wolff-Parkinson-White Syndrome in the Closed Heart Using Cryosurgery: A Simplified Approach," JACC 3(2): 405-409, 1984.

Randall et al., "Local Epicardial Chemical Ablation of Vagal Input to Sino-Atrial and Atrioventricular Regions of the Canine Heart," Journal of the Autonomic Nervous System 11:145-159, 1984.

Guiraudon et al., "Surgical Ablation of Posterior Septal Accessory Pathways in the Wolf-Parkinson-White Syndrome by a Closed Heart Technique," Journal Thoracic Cardiovascular Surgery 92:406-413, 1986.

Gallagher et al., "Surgical Treatment of Arrhythmias," The American Journal of Cardiology 61:27A-44A, 1988.

Mahomed et al., "Surgical Division of Wolff-Parkinson-White Pathways Utilizing the Closed-Heart Technique: A 2-Year Experience in 47 Patients," The Annals of Thoracic Surgery45(5): 495-504, 1988.

Cox et al., Surgery for Atrial Fibrillation: Seminars in Thoracic and Cardiovascular Surgery, vol. 1 No. 1 (Jul. 1989) pp. 67-73.

Bredikis and Bredikis; Surgery of Tachyarrhythmia: Intracardiac Closed Heart Cryoablation; PACE, vol. 13, pp. 1980-1984.

McCarthy et al., "Combined Treatment of Mitral Regurgitation and Atrial Fibrillation with Valvuloplasty and the Maze Procedure," The American Journal of Cardiology 71: 483-486, 1993.

Yamauchi et al. "Use of Intraoperative Mapping to Optimize Surgical Ablation of Atrial Flutter," The Annals of Thoracic Surgery 56: 337-342, 1993.

Graffigna et al., "Surgical Treatment of Wolff-Parkinson-White Syndrome: Epicardial Approach Without the Use of Cardiopulmonary Bypass," Journal of Cardiac Surgery 8: 108-116, 1993.

Siefert et al., "Radiofrequency Maze Ablation for Atrial Fibrillation," Circulation 90(4): I-594.

Surgical treatment of artial fibrillation: a reveiw; Europace (2004) 5, S20-S29.

Cox et al., "Modification of the Maze Procedure for Atrial Flutter and Atrial Fibrillation. I. Rational and Surgical Results," The Journal of Thoracic Cardiovascular Surgery 110: 473-484. 1995.

Cox, "The Maze III Procedure for Treatment of Atrial Fibrillation," Sabiston DC, ed Atlas of Cardiothoracic Surgery, Philadelphia: WB Saunders: 460-475, 1994.

Sueda et al., "Simple Left Atrial Procedure for Chronic Atrial Fibrillation Associated with Mitral Valve Disease," The Annals of Thoracic Surgery 62(6): 1796-1800, 1996.

Tsui et al., "Maze 3 for Atrial Fibrillation: Two Cuts Two Few?" PACE 17:2163-2166, 1994.

Kosakai et al., "Cox Maze Procedure for Chronic Atrial Fibrillation Associated with Mitral Valve Disease," The Journal of Thoracic Cardiovascular Surgery 108: 1049-1055, 1994.

Cox et al., "The Surgical Treatment of Atrial Fibrillation, IV Surgical Technique," J of Thorac Cardiovasc Surg, 1991: 101: 584-593.

Nardella, "Radio Frequency Energy and Impedance Feedback," SPIE vol. 1068, Catheter Based Sensing and Imaging Technology (1989).

Sie et al., "Radiofrequency Ablation Fibrillation in Patients Undergoing Mitral Valve Surgery. First Experience," Circulation (Nov. 1996) 96:450,I-675,#3946.

Sie et al., "Radiofrequency Ablation of Atrial Fibrillation In Patients Undergoing Valve Surgery,"Circulation (Nov. 1997) 84:I450,#2519.

Jais et al., "Catheter Ablation for Paroxysmal Atrial Fibrillation: High Success Rates with Ablation in the Left Atrium," Circulation ( Nov. 1996) 94:I-675,#3946.

Cox, "Evolving Applications of the Maze Procedure for Atrial Fibrillation," Ann Thorac Surg, 1993;55:578-580.

Cox et al. "Five-Year Experience with the Maze Procedure for Atrial Fibrillation," Ann Thorac Surg, 1993; 56:814-824.

Avitall et al., "New Monitoring Criteria for Transmural Ablation of Atrial Tissues,"Circulation, 1996;94(Supp 1):I-493,#2889.

Cox et al., "An 8 1/2 Year Clinical Experience with Surgery for Atrial Fibrillation," Annals of Surgery, 1996;(3):267-275.

Haissaguerre et al., "Radiofrequency Catheter Ablation for Paroxysmal Atrial Fibrillaition in Humans: Elaboration of a procedure based on electrophysiological data," Nonpharmacological Management of Atrial Fibrillation, 1997 pp. 257-279.

Haissaguerre et al., "Right and Left Atrial Radiofrequency Catheter Therapy of Paroxysmal Atrial Fibrillation," Journal of Cardiovascular Electrophysiology, 1996;7(12):1132-1144.

Haissaguerre et al., "Role of Catheter Ablation for Atrial Fibrillation," Current Opinion in Cardiology, 1997;12:18-23.

Kawaguchi et al., "Risks and Benefits of Combined Maze Procedure for Atrial Fibrillation Associated with Organic Heart Disease," JACC, 1996,28(4):985-990.

Cox, et al., "Perinodal cryosurgery for atrioventricular node reentry tachycardia in 23 patients," Journal of Thoracic and Cardiovascular Surgery, 99:3, Mar. 1990, pp. 440-450.

Cox, "Anatomic-Electrophysiologic Basis for the Surgical Treatment of Refractory Ischemic Ventricular Tachycardia," Annals of Surgery, Aug. 1983; 198:2;119-129.

Williams, et al., "Left atrial isolation," J Thorac Cardiovasc Surgp; 1980; 80: 373-380.

Scheinman, "Catheter-based Techniques for Cure of Cardiac Arrhythmias," Advances in Cardiovascular Medicine, 1996, ISSN 1075-5527, pp. 93-100.

Sueda et al., "Efficacy of a Simple Left Atrial Procedure for Chronic Atrial Fibrillation in Mitral Valve Operations," Ann Thorac Surg, 1997;63:1070-1075.

Sueda et al., "Simple Left Atrial Procedure for Chronic Atrial Fibrillation Associated with Mitral Valve Disease," The Society of Thoracic Surgeons, 1996;62:1796-1800.

* cited by examiner

METHOD FOR INTERRUPTING CONDUCTION PATHS WITHIN THE HEART

CROSS-REFERENCE TO RELATED APPLICATIONS

This is a continuation of application Ser. No. 10/277,144, filed Oct. 21, 2002 (now abandoned), which is a continuation of application Ser. No. 09/583,303, filed May 30, 2000 (now U.S. Pat. No. 6,502,575), which is a divisional of application Ser. No. 09/180,124 filed Nov. 2, 1998 (now U.S. Pat. No. 6,165,174), which is the U.S. national phase of PCT application No. PCT/NL97/00223 filed Apr. 25, 1997, which claims priority from Netherlands application No. 1003021, filed May 3, 1996.

FIELD OF THE INVENTION

The invention relates to an instrument for making at least one transmural lesion in one or more walls of the atria of the heart, which lesion essentially blocks the electrical impulse conduction in a direction crosswise to the transmural lesion.

BACKGROUND OF THE INVENTION

All kinds of heart arrhythmias, and in particular chronic and paroxysmal atrial fibrillation, can currently be treated by surgery.

A known surgical procedure (MAZE) was designed to eliminate atrial fibrillation permanently. In this procedure incisions are made with a scalpel in the walls of the atria, in order to block electrical impulse conduction in a direction crosswise to the incisions, by the interruption of the tissue continuity. As a result of the subsequent scarring, these electrical blocks acquire a permanent character.

This known technique is as yet performed only to a limited extent worldwide, owing to the complexity of the operation. The increased risk is particularly associated with the duration of the operation and the way in which the operation has to be carried out.

The duration of the operation, and in particular the cross-clamp time (x-clamp) is so long that there is a great risk of damage to the heart muscle.

The cross-clamp time required for the MAZE procedure alone is currently still an average of 68 min. (range 50–102 min.), and the necessary time on the heart-lung machine is on average 182 min. (range 130–256 min.). For further data you are referred to Atrial Fibrillations: Mechanisms and Therapeutic Strategies, Futura Publishing Co. Inc. Armonk, N.Y. 1994. J. L. Cox: Surgical Interruption of Atrial Reentry as a Cure for Atrial Fibrillation. The way in which the operation is performed with the scalpel produces an increased risk of vascular suture leaks and subsequent bleeding, due to the large number and location of the vascular sutures involved.

SUMMARY OF THE INVENTION

The object of the present invention is to provide an instrument of the abovementioned type which eliminates the abovementioned disadvantages, and which in particular shortens the time required for the operation and reduces the risk of bleeding and damage, therefore reducing the risk for the patient in open-heart surgery.

According to the invention, the instrument indicated is characterized in that the instrument is a probe in which the end which during the operation comes into contact with the wall to be treated is a closed electrode which can interact with an RF power source, while the probe is of a relatively rigid type.

The instrument according to the invention is a probe by means of which in open-heart surgery it is possible to make a permanent change in an atrial wall which is transmural, i.e. it extends over the entire thickness of the wall.

As will be discussed at a later stage, during the performance of the operation the electrode at the end of the probe is brought into contact with the atrial wall to be treated and is moved along it in a linear pattern. On excitation of the electrode with RF power, dielectric (RF) heating of the wall tissue occurs. The RF treatment produces a change in the cell structure of the atrial wall, with the result that electrical impulse conduction in a direction crosswise to the transmural lesion is blocked.

In order to be able to work well with it, the probe must be of a relatively rigid type, so that the electrode can be accurately positioned on and moved along the atrial wall. In the operation no disintegration of the tissue of the atrial wall occurs, and there is no risk of subsequent bleeding. The operation can be carried out on the outside or the inside of the atrium as desired.

Methods of RF heating or dielectric heating are based on the use of heat generated in materials which are relatively poor electrical conductors when they are placed in high-frequency electromagnetic fields. The heat is generated as a result of dielectric losses occurring in a material situated between metal electrodes which form a capacitor which is connected to a high-frequency (RF) generator. Such heating is highly uniform and therefore extremely suitable for use of the instrument, the probe, according to the invention. During use of the probe, one of the capacitor "plates" is formed by the electrode at the end of the probe, while the other "plate" is a counter-electrode which is stuck on, for example, the patient's back; when the latter electrode is being placed, it is preferable to use a contact gel which has electrical conductance. Of course, the counter-electrode can also be placed on the outside of the atrial wall of the heart, for example if the electrode of the probe is being brought into contact with the inside of said wall.

In connection with the invention, reference is made to WO 95/03742, which discloses a catheter comprising at the distal a metal electrode by means of which tissue erosion, also known as ablation, can be carried out.

Such a catheter typically has a length of approximately 1 meter, a diameter of approximately 2 mm, and has an electrode of approximately 2 mm diameter, and its low thickness makes it very flexible, so that it can follow a blood vessel without any problems. This catheter is suitable for local punctate ablation. Such a catheter is not suitable for use as a probe for making stripe-shaped transmural lesions in an atrial wall.

In particular, the probe according to the invention has at least a handle; an end; a relatively rigid member, such as a shaft, between the handle and the end, and connecting and conduction means for connecting the end of the probe to an RF power source.

In the instrument according to the invention a temperature recorder is advantageously present near the end of the probe, which temperature recorder, operating in a feedback system with the RF power source, can regulate the temperature of the end of the probe to a preset value. Through input of the RF power, the temperature of the end of the probe will generally rise; feedback with the RF power source makes it possible to ensure that the temperature of the end does not exceed a predetermined value.

With use of RF power it is extremely important that the fewest possible electrical blockages should be present in the body section between the end of the probe and the counter-electrode on the outside of the body. On account of this, it is preferable to ensure that the probe can interact with means for supplying a physiologically acceptable liquid to the end thereof. In its simplest form, such a liquid is supplied near the electrode of the probe by way of a line which does not form part of the probe. The function of the liquid is, on the one hand, to cool the electrode and, on the other, to prevent the occurrence of electrically insulating air gaps which adversely affect the efficiency of the RF action.

It is very advantageous for the probe according to the invention itself to have means for discharging a physiologically acceptable liquid near the end of the probe. Said liquid will generally preferably have a certain degree of electrical conduction, and is expediently a physiological salt solution.

In a very attractive embodiment, the instrument has between the handle of the probe and the shaft inlet means for introducing the physiologically acceptable liquid, which inside the shaft remains electrically insulated from the connecting and conduction means present in the shaft, while near the end it has outflow means for the physiologically acceptable liquid. With this embodiment, the functioning of the probe can be improved yet further, and it can be ensured that the greatest RF energy effect is concentrated in the wall of the atrium to be treated, forming the desired transmural lesion.

At the side of the handle facing away from the end of the probe, the conduction and connecting means of the probe according to the invention comprise a connector connected thereto, with contact means for connection of the electrode to the end of the probe and the temperature recorder present therein to the RF power source.

The connector is preferably of the rapid coupling type, so that easy coupling to the RF power source is permitted.

In order to make handling of the instrument according to the invention, in the form of a probe, as easy as possible for the operating surgeon during an open-heart operation, the shaft of the probe preferably has an intrinsic curvature, which is expediently approximately 140 degrees.

BRIEF DESCRIPTION OF THE DRAWINGS

The invention will now be explained with reference to the drawing, in which.

DETAILED DESCRIPTION OF THE DRAWINGS

Figure 1:
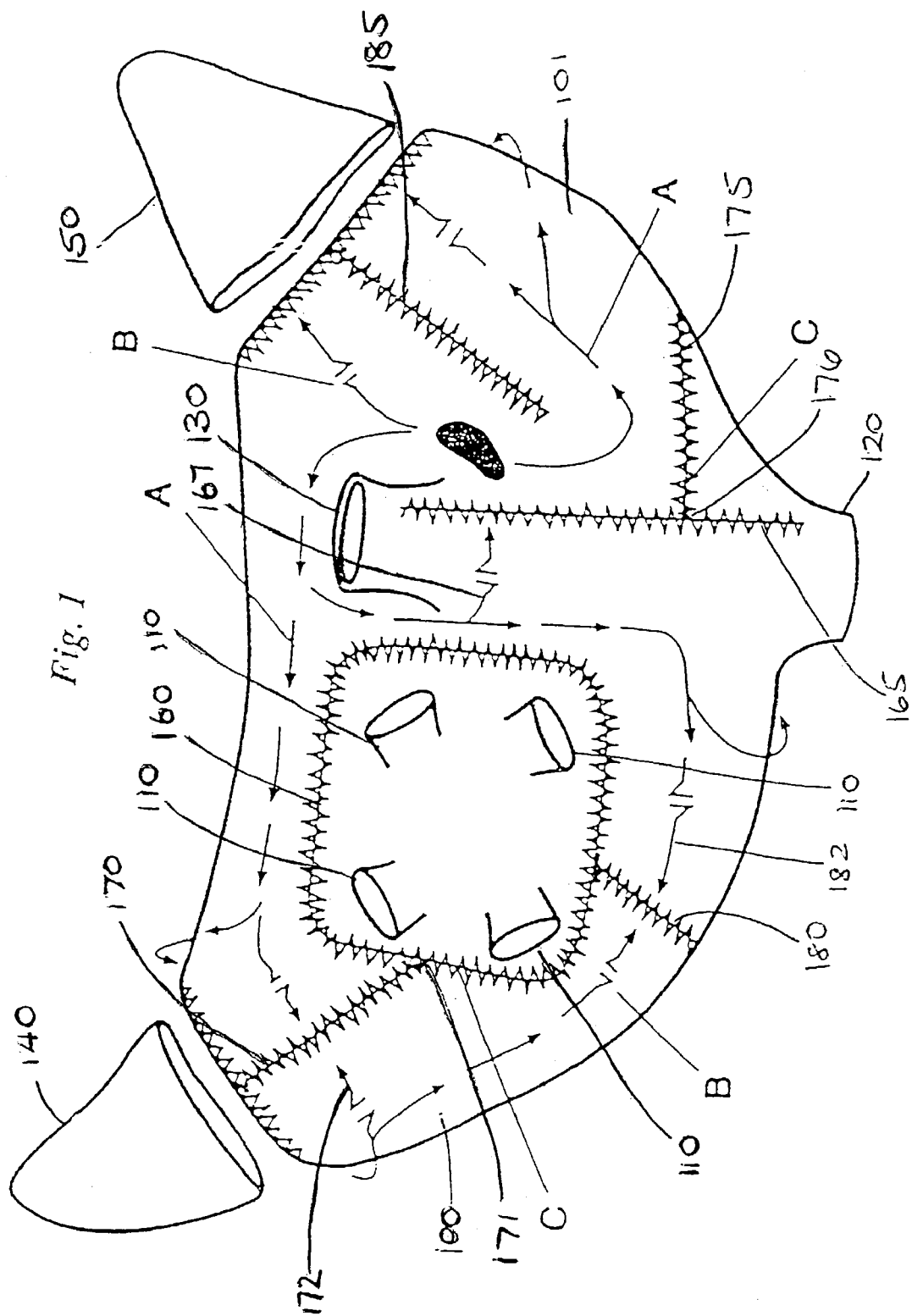
FIG. 1 shows a schematic picture of the transmural lesions which can be made with the instrument according to the invention, and which can block electrical impulses in directions crosswise to said lesions.

FIG. 1 shows diagrammatically in a two-dimensional view the two atria of a human heart, in which the transmural lesions are indicated by reference letter C, the undisturbed electrical impulses by A, and the blocked electrical impulses by B. The lesions C are in the nature of scar tissue which is formed after treatment using the probe according to the invention. The atria, as viewed epicardially, include the left atrium 100 and the right atrium 101. Structural features of the atria include the pulmonary veins 110, the inferior vena cava 120, the superior vena cava 130, the left atrial appendage 140 and the right atrial appendage 150. A first lesion 160 is a curved lesion that is joined end-to-end such that it encircles the pulmonary veins 110, and is between the pulmonary veins 110 and conductive pathways in the left atrium 100 and between the pulmonary veins 110 and conductive pathways in the right atrium 101. A second lesion 165 extends between the superior vena cava 130 and the inferior vena cava 120 and blocks a first conductive pathway 167. A third lesion 170 extends across the left atrium 100 from an intersection 171 with a portion of the first lesion 160 toward the left atrial appendage 140 and blocks a second conductive pathway 172. A fourth lesion 175 extends along the right atrium 101 laterally from an intersection 176 with a portion of the second lesion 165. A fifth lesion 180 extends from a portion of the first lesion 160 along the left atrium 100 and blocks a third conductive pathway 182. A sixth lesion 185 extends along the right atrium 101 toward the right atrial appendage 150.

Figure 2:
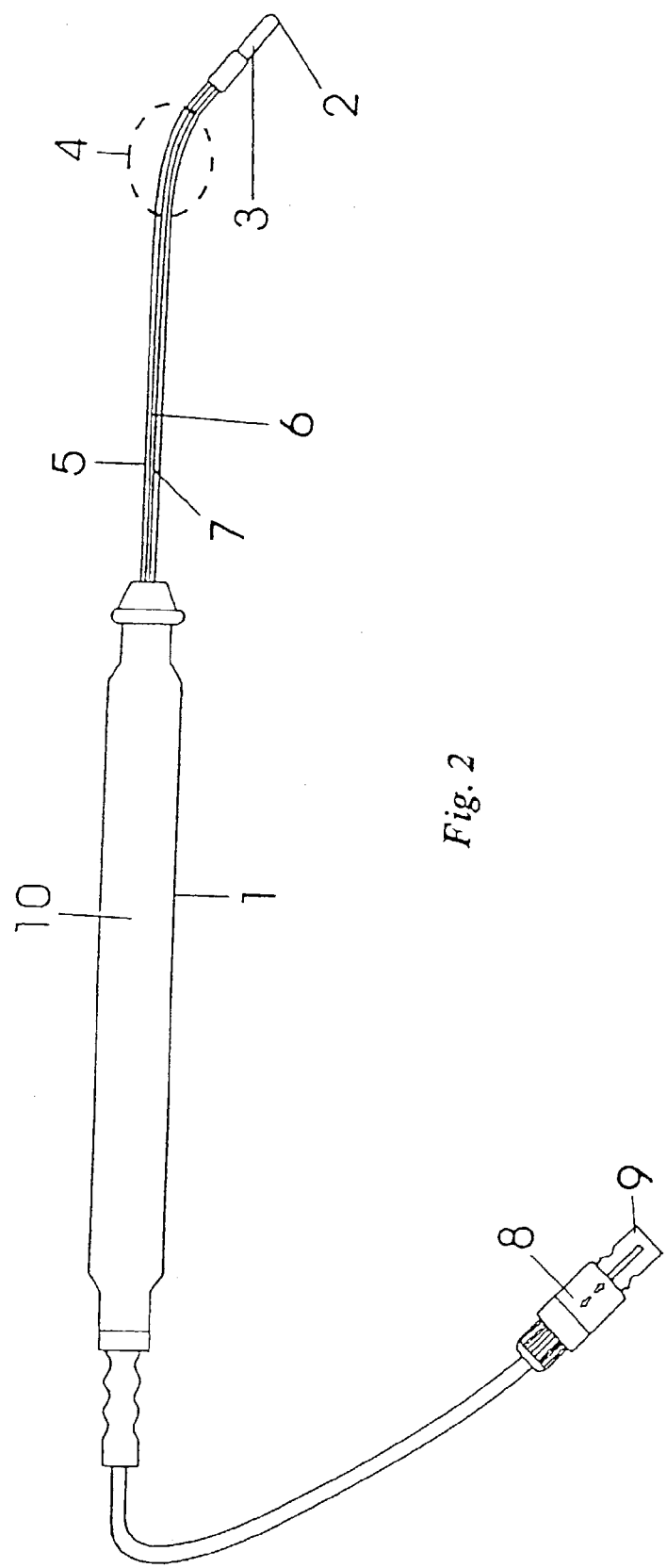
FIG. 2 shows an instrument according to the invention in a first embodiment.

FIG. 2 shows a probe according to the invention in a first embodiment, and shows a handle 1, an active metal end 2 as a closed electrode with indication of the position of a temperature sensor 3. The shaft of the probe 5 has a curvature 4 of approximately 140 degrees, and inside the shaft run the electrical wires 6 for exciting the closed electrode-type end 2 and wire 7 for connecting the temperature sensor which is fitted at the position of reference number 3.

Inside the handle 1 are electrical switch means 10 (not shown in any further detail) for permitting connection of the probe to the RF generator (not shown). Reference numbers 8 and 9 also indicate a connector making it possible to couple the probe to the RF 5 generator.

Figure 3:
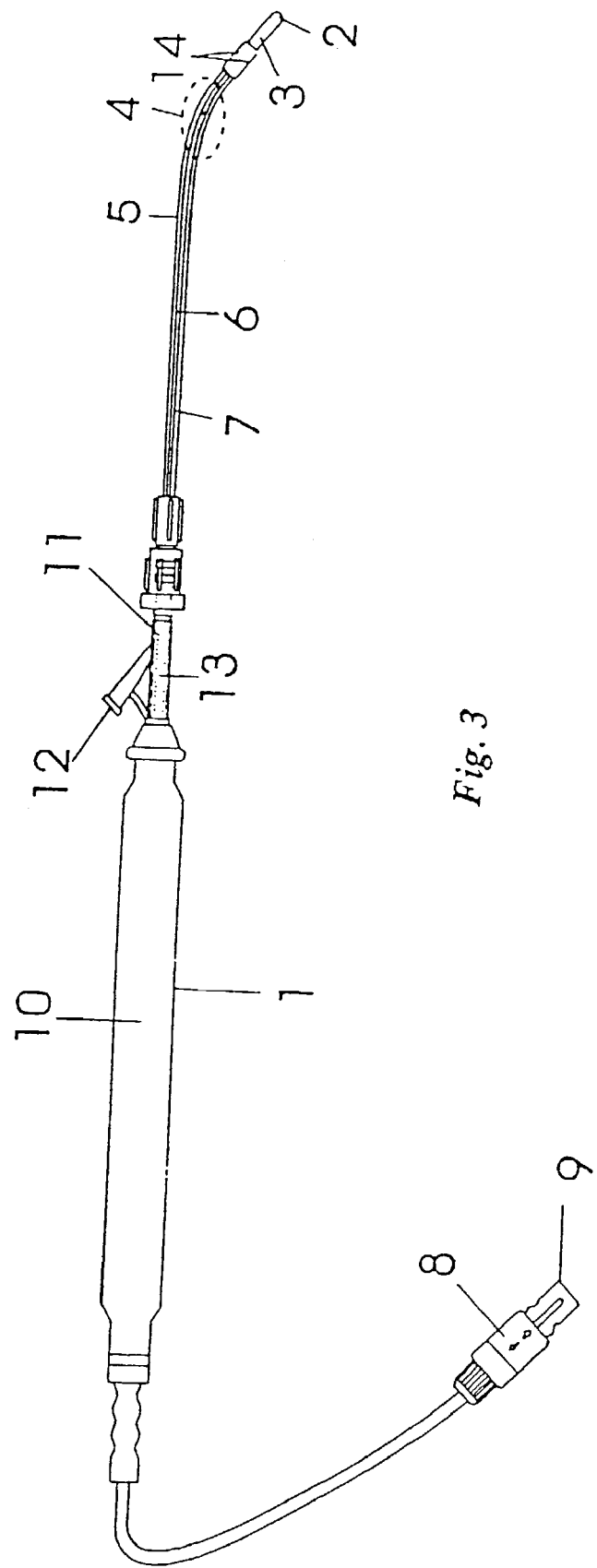
FIG. 3 shows an instrument according to the invention in a second embodiment.

FIG. 3 shows a particularly advantageous embodiment of the probe according to the invention, which is identical to the probe of FIG. 2, but in which reference number 11 indicates a Y-connector which makes it possible to supply a physiologically acceptable liquid by way of a port 12 into the shaft 5, said physiologically acceptable liquid being guided through the shaft 5 without contact with the conduction means 6 and 7. The physiologically acceptable solution flows by way of the port 12 to an inner shaft 13, and from there by way of the shaft 5 to the outflow ports 14 which are disposed in the vicinity of the metal end 2. The physiologically acceptable liquid is expediently a physiological salt solution which is readily tolerated by the body.

The physiological salt solution, on the one hand, achieves cooling of the closed electrode 2 and, on the other hand, lowers the electrical resistance between the closed electrode of the end 2 and the atrial wall. Extremely good and reproducible results are obtained with the probe shown in the figure. The source of RF power is typically a generator which can deliver a power of, for example, maximum 50 watt at a frequency of 500 kHz. The power supplied is a function of the temperature set and the tissue contact of the electrode forming the end of the probe. The desired temperature can be set at the generator, and in general lies in the range 50 to 70 degrees C. If temperatures higher than the given range are permitted, burning of the tissue (coagulation) will occur, with the result that an insulating layer is formed; said layer will make further action of the RF energy difficult, with the result that underlying tissue is not treated fully, if at all.

The end 2 of the probe expediently comprises platinum and is typically a cylindrical shape with a diameter of 4 mm. The diameter can generally lie between 3 and 6 mm.

The total length of the probe without connection means is typically approximately 35 cm, the handle being approximately 20 cm long, the shaft approximately 10 cm, and the end approximately 2 cm. In general, the length of the shaft 5 lies between 8 and 15 cm, and the shaft has a diameter between 3 and 6 mm and is made of a physiologically acceptable plastic. Suitable plastics are nylon 66, polypropylene and high-density polyethylene.

The invention claimed is:

1. A method of creating an arrhythmia in the heart of a patient by ablative treatment of the atrium of the heart comprising:
   (a) providing a surgical instrument having a handle and a first electrode affixed to the handle;
   (b) providing a second electrode;
   (c) providing a power source in electrical connection with the first and second electrodes;
   (d) performing an open-heart surgical procedure in which a first electrode is placed proximal to a first portion of a wall of the atrium and the second electrode is placed proximal to a second portion of the wall of the atrium such that one of the first and second electrodes is on the inside of the atrium and the other of the first and second electrodes is on the outside of the atrium;
   (e) transferring energy from the power source to the first electrode to cause a transmural lesion to form in the wall of the atrium between the first and second electrodes.

2. The method of claim 1, further comprising:
   (f) moving the first electrode to another portion of the wall of the atrium;
   (g) transferring energy from the power source to the first electrode to cause a transmural lesion to form in the another portion of the wall of the atrium; and
   (h) repeating (f) to (g) to form at least one elongated, continuous transmural lesion in the atrium.

3. The method of claim 1, wherein the first electrode has an elongated shape.

4. The method of claim 1, further comprising monitoring the temperature of the first electrode.

5. The method of claim 4, wherein the temperature of the first electrode during the transfer of electrical energy is limited to a regulated preset value in the range of 50 to 70 degrees C.

6. The method of claim 1, further comprising delivering a physiologically acceptable liquid to the wall of the atrium.

7. The method of claim 6, wherein the physiologically acceptable liquid is a salt solution.

8. The method of claim 1, wherein the power source provides RF energy to the first electrode.

9. The method of claim 2, wherein the elongated, continuous transmural lesion encircles at least one pulmonary vein.

10. The method of claim 9, wherein the first electrode is moved to form a second, transmural lesion intersecting with the encircling lesion.

11. The method of claim 9, wherein the encircling lesion encircles all of the heart's pulmonary veins.

12. The method of claim 9, wherein a portion of the encircling lesion is formed between a pulmonary vein and conductive pathways in the right atrium.

13. The method of claim 9, wherein a portion of the encircling lesion is formed between a pulmonary vein and conductive pathways in the left atrium.

14. The method of claim 10, wherein the second lesion formed extends across the left atrium toward the left atrial appendage.

15. The method of claim 2, wherein the first electrode as moved along the atrial wall without lifting the first electrode away from the wall.

16. A method of treating an arrythmia in the heart of a patient by ablative treatment of the atrium of the heart comprising:
   (a) providing a surgical instrument having a handle with a first electrode affixed to the handle and a fluid outlet;
   (b) providing a second electrode;
   (c) providing a power source in electrical connection with the first and second electrodes;
   (d) performing an open-heart surgical procedure in which the first electrode is placed proximal to a first portion of a wall of the atrium and the second electrode is placed proximal to a second portion of the wall of the atrium such that one of the first and second electrodes is on the inside of the atrium and the other of the first and second electrodes is on the outside of the atrium;
   (e) transferring a physiologically acceptable liquid to the fluid outlet;
   (f) transferring energy from the power source to the first electrode to cause a transmural lesion to form in the wall of the atrium between the first and second electrodes.

17. The method of claim 16, further comprising:
   (g) moving the first electrode to another portion of the wall of the atrium;
   (h) transferring energy from the power source to the first electrode to cause a transmural lesion to form in the another portion of the wall of the atrium; and
   (i) repeating (g) to (h) to form at least one elongated, continuous transmural lesion in the atrium.

18. The method of claim 16, wherein the first electrode has an elongated shape.

19. The method of claim 16, further comprising monitoring the temperature of the first electrode.

20. The method of claim 19, wherein the temperature of the first electrode during the transfer of electrical energy is limited to a regulated preset value in the range of 50 to 70 degrees C.

21. The method of claim 16, wherein the physiologically acceptable liquid is a salt solution.

22. The method of claim 16, wherein the power source provides RF energy to the first electrode.

23. The method of claim 17, wherein the elongated, continuous transmural lesion encircles at least one pulmonary vein.

24. The method of claim 23, wherein the first electrode is moved to form a second, transmural lesion intersecting with the encircling lesion.

25. The method of claim 23, wherein the encircling lesion encircles all of the heart's pulmonary veins.

26. The method of claim 23, wherein a portion of the encircling lesion is formed between a pulmonary vein and conductive pathways in the right atrium.

27. The method of claim 23, wherein a portion of the encircling lesion is formed between a pulmonary vein and conductive pathways in the left atrium.

28. The method of claim 24, wherein the second lesion formed extends across the left atrium toward the left atrial appendage.

29. The method of claim 17, wherein the first electrode is moved along the atrial wall without lifting the first electrode away from the wall.

* * * * *

UNITED STATES PATENT AND TRADEMARK OFFICE
CERTIFICATE OF CORRECTION

PATENT NO. : 7,128,740 B2 Page 1 of 1
APPLICATION NO. : 10/405392
DATED : October 31, 2006
INVENTOR(S) : Jacobs et al.

It is certified that error appears in the above-identified patent and that said Letters Patent is hereby corrected as shown below:

Column 5, line 9, that portion of the claim reading "of creating an" should read --of treating an--.

Column 6, line 1, that portion of the claim reading "electrode as moved" should read --electrode is moved--.

Signed and Sealed this

First Day of May, 2007

JON W. DUDAS
*Director of the United States Patent and Trademark Office*